(12) United States Patent
Neenan et al.

(10) Patent No.: US 6,268,126 B1
(45) Date of Patent: **\*Jul. 31, 2001**

(54) ANTIVIRAL POLYMERS COMPRISING ACID FUNCTIONAL GROUPS AND HYDROPHOBIC GROUPS

(75) Inventors: Thomas X. Neenan, Boston; W. Harry Mandeville, III, Lynnfield, both of MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/491,008

(22) Filed: Jan. 25, 2000

Related U.S. Application Data

(63) Continuation of application No. 08/934,313, filed on Sep. 19, 1997, now Pat. No. 6,060,235.

(51) Int. Cl.$^7$ .............................. C12Q 1/70; A61K 31/74; A61K 31/785; C08F 116/34
(52) U.S. Cl. .............................. 435/5; 424/78; 424/78.27; 424/78.35; 526/315
(58) Field of Search .................................. 435/5; 424/78, 424/78.27, 78.35; 526/315

(56) References Cited

U.S. PATENT DOCUMENTS

| | | | |
|---|---|---|---|
| 3,224,941 | 12/1965 | Nash et al. | 167/55 |
| 3,466,365 | 9/1969 | Schlesinger | 424/78 |
| 3,624,218 | 11/1971 | Regelson | 424/78 |
| 3,812,248 | 5/1974 | Regelson | 424/78 |
| 3,859,433 | 1/1975 | Regelson | 424/85 |
| 3,893,890 | 7/1975 | Wurzburg et al. | 195/104 |
| 3,956,480 | 5/1976 | Dichter et al. | 424/54 |
| 3,996,347 | 12/1976 | Breslow et al. | 424/78 |
| 4,150,238 | 4/1979 | Burg et al. | 560/205 |
| 4,223,109 | 9/1980 | Wolgemuth | 525/327 |
| 4,361,547 | 11/1982 | Sipos et al. | 424/56 |
| 4,604,404 | 8/1986 | Munson, Jr. et al. | 514/494 |
| 4,762,715 | 8/1988 | Lukas et al. | 424/145 |
| 4,783,446 | 11/1988 | Neushul | 514/54 |
| 5,149,523 | 9/1992 | Lundberg et al. | 424/78.1 |
| 5,152,978 | 10/1992 | Baba et al. | 424/78.27 |
| 5,211,944 | 5/1993 | Tempesta | 424/78.08 |
| 5,290,894 | 3/1994 | Melrose et al. | 526/315 |
| 5,292,505 | 3/1994 | Baba et al. | 424/78.08 |
| 5,308,612 | 5/1994 | Lee | 424/78.35 |
| 5,346,695 | 9/1994 | Nonoyama et al. | 424/78.08 |
| 5,424,063 | 6/1995 | Cardin et al. | 424/78.08 |
| 5,510,103 | 4/1996 | Yokoyama et al. | 424/78.08 |
| 5,571,505 | 11/1996 | Cardin et al. | 424/78.08 |
| 5,670,143 | 9/1997 | Cardin et al. | 424/78.08 |
| 5,670,144 | 9/1997 | Cardin et al. | 424/78.08 |
| 6,060,235 | * 5/2000 | Neenan et al. | 435/5 |

FOREIGN PATENT DOCUMENTS 2 090 605   7/1982   (GB).
93/14146    7/1993   (WO).

OTHER PUBLICATIONS

Mohan, P., et al., "Sulfonic acid polymers as a new class of human immunodeficiency virus inhibitors," *Antiviral Research*, 18:139–150 (1992).

Tan, G.T., et al., "Sulfonic acid polymers are potent inhibitors of HIV–1 induced cytopathogenicity and the reverse transcriptases of both HIV–1 and HIV–2," *Biophys. Acta*, 1181:183–188 (1993).

Baba, M., et al., "Novel Sulfated Polymers as Highly Potent and Selective Inhibitors of Human Immunodeficiency Virus Replication and Giant Cell Formation," *Antimicrob. Agents Chemother.*, 34(1):134–138 (1990).

Neyts, J. and De Clercq, E., "Effect of Polyanionic Compounds on Intracutaneous and Intravaginal Herpesvirus Infection in Mice: Impact on the Search for Vaginal Microbicides with Anti–HIV Activity," *Journal of Acquired Immune Deficiency Syndromes and Human Retrovirology*, 10:8–12 (1995).

Taylor, D.L., et al., "Novel Sulphonic Acid Polymers as Inhibitors of HIV Host–Cell Interactions," IXth Internat'l Conference on AIDS, Jun. 6–11, 1993, Abstract PO–B26–2071.

Baba, M. et al., "Pentosan polysulfate, a sulfated oligosaccharide, is a potent and selective anti–HIV agent in vitro," *Antiviral Research*, 9:335–343 (1988).

Cushman, M., et al., "Preparation and Anti–HIV Activities of Aurintricarboxylic Acid Fractions and Analogues: Direct Correlation of Antiviral Potency with Molecular Weight," *J. Med. Chem.*, 34:329–337 (1991).

Ito, M., et al., "Inhibitory effect of dextran sulfate and heparin on the replication of human immunodeficiency virus (HIV) in vitro," *Antiviral Research*, 7:361–367 (1987).

Leydet, A., et al., "Polyanion Inhibitors of Human Immunodeficiency Virus and Other Viruses. 1. Polymerized Anionic Surfactants," *J. Med. Chem.*, 38:2433–2440 (1995).

Leydet, A., et al., "Polyanion Inhibitors of Human Immunodeficiency Virus and Other Viruses. Part 2. Polymerized Anionic Surfactants Derived from Amino Acids and Dipeptides," *J. Med. Chem.*, 39:1626–1634 (1996).

Leydet, A., et al., "Polyanion inhibitors of human immunodeficiency virus. Part III. Polymerized anionic surfactants derived from D–glucose," *Recl. Trav. Chim. Pays–Bas*, 115:421–426 (1996).

(List continued on next page.)

Primary Examiner—Hankyel T. Park
(74) Attorney, Agent, or Firm—Hamilton, Brook Smith & Reynolds, P.C.

(57) ABSTRACT

The present invention relates to a method of treating a viral infection in an animal, such as a human, by administering to the animal a therapeutically effective amount of a polymer comprising a plurality of pendant hydrophobic groups and a plurality of pendant acid functional groups. The acid functional groups are connected directly to the polymer backbone or via an aliphatic spacer group of 1 to about 20 atoms in length.

21 Claims, No Drawings

OTHER PUBLICATIONS

Leydet, A., et al., "Polyanion Inhibitors of Human Immunodeficiency Virus. Part IV. Polymerized Anionic Surfactants: Influence of the Density and Distribution of Anionic Groups on the Antiviral Activity," *Bioorg. Med. Chem. Lett.*, 6:397–402 (1996).

Leydet, A., et al., "Polyanion Inhibitors of Human Immunodeficiency Virus and Other Viruses. 5. Telomerized Anionic Surfactants Derived from Amino Acids," *J. Med. Chem.*, 40:342–349 (1997).

Leydet A., et al., "Polyanion Inhibitors of Human Immunodeficiency Virus and Other Viruses. 6. Micelle–like AntiHIV Polyanionic Compounds Based on a Carbohydrate Core," *J. Med. Chem.*, 40:350–356 (1997).

* cited by examiner

ANTIVIRAL POLYMERS COMPRISING ACID FUNCTIONAL GROUPS AND HYDROPHOBIC GROUPS

RELATED APPLICATION

This application is a continuation of U.S. application Ser. No. 08/934,313, filed Sep. 19, 1997, U.S. Pat. No. 6,060,235, the entire teachings of which are incorporated herein by reference.

BACKGROUND OF THE INVENTION

One mechanism for infection of a host cell by a microbe, such as a virus, a bacterium or a protozoan, proceeds via initial attachment of the microbe to the host cell surface. This process is mediated by relatively weak attractive interactions between adhesion molecules on the surfaces of the microbe and the host cell. In general, microbe-host cell attachment is the product of a multiplicity of such interactions, via what has been referred to as the polyvalent effect. One well-studied example of such a process is the attachment of the influenza A virus to mammalian epithelial cells, which results from interaction of terminal N-acetylneuraminic acid groups of glycolipids and glycoproteins on the host cell surface with the attachment glycoprotein hemagglutinin on the viral surface.

The scarcity of effective antiviral agents points to the need for new approaches to the treatment of viral infections. The attachment step is an attractive target for such a treatment, and much activity has focused on the development of N-acetylneuraminic acid-containing compounds capable of binding to viral hemagglutinin, thus inhibiting viral attachment to host cells. Studies have demonstrated that polyvalent compounds, such as polymers bearing pendant N-acetylneuraminic acid groups, bind influenza virus with association constants which are several orders of magnitude higher than those of monomeric N-acetylneuraminic acid derivatives. To date, no polyvalent N-acetylneuraminic acid containing compounds are in clinical use for treatment or prevention of influenza. Moreover, no data demonstrating in vivo efficacy of such compounds have yet been published.

A disadvantage of N-acetylneuraminic acid-functionalized compounds as therapeutic agents for the treatment of infection by influenza A virus and, possibly, other viruses, is the great expense of this sugar. In addition, the influenza virus has at its surface the enzyme neuramidinase, which cleaves N-acetylneuraminic acid moieties from such molecules, eventually destroying their ability to bind the virus. There is, thus, a need for inhibitors of viral attachment to mammalian cells which have an improved efficacy, are readily prepared from inexpensive starting materials and have a broad spectrum of activity.

SUMMARY OF THE INVENTION

The present invention relates to a method of treating a viral infection in an animal, such as a human, by administering to the animal a therapeutically effective amount of a polymer having a plurality of pendant hydrophobic groups and pendant acid functional groups which are directly attached to the polymer backbone or attached to the polymer backbone by an aliphatic spacer group. The aliphatic spacer group can have a length in the range from 1 to about 20 atoms.

Suitable acid functional groups include carboxylic acid, sulfonic acid, phosphonic acid, hydrosulfate and boronic acid groups. The acid groups can also be present in the conjugate base form. Suitable hydrophobic groups include normal or branched $C_2$–$C_{20}$-alkyl groups, arylalkyl groups and aryl groups.

In one embodiment, the polymer to be administered comprises a monomer or repeat unit having an acid functional group and a hydrophobic group. In another embodiment, the polymer is a copolymer comprising an acid-functionalized monomer and a hydrophobic monomer. The polymer to be administered can, optionally, further include a monomer comprising a neutral hydrophilic group, such as a hydroxyl group or an amide group.

The present method has several advantages. For example, the polymers employed are easily prepared using standard techniques of polymer synthesis and inexpensive starting materials. The polymers will not be substantially degraded in the gastrointestinal tract and, therefore, can be administered orally. Polymer compositions can also be readily varied, to optimize properties such as solubility or water swellability and antiviral activity. Finally, the polymers to be administered include acid functional groups attached to the polymer backbone via aliphatic spacer groups. The structural flexibility of such spacer groups minimizes backbone constraints on the interaction of the acid groups with viral targets.

DETAILED DESCRIPTION OF THE INVENTION

The present invention relates to a method of treating a viral infection in an animal, such as a human, by administering to the animal a therapeutically effective amount of a polymer comprising a plurality of pendant acid functional groups and pendant hydrophobic groups. The acid functional group can be directly bonded to the polymer backbone or separated from the polymer backbone by an aliphatic spacer group having a length of from 1 to about 20 atoms.

The polymer can be administered in the acid form, in which all acidic groups are protonated or in the conjugate base form, wherein the acidic functional groups are deprotonated and carry a negative charge. In the conjugate base form the negative charge of the polymer will be balanced by a suitable number of counter cations, such as alkali metal ions, for example, sodium, potassium or cesium ions, alkaline earth metal ions, such as magnesium ions, or tetraalkylammonium ions. The polymer can also be administered in a partially deprotonated form, in which the extent of deprotonation is less than 100%.

As used herein, a "therapeutically effective amount" is an amount sufficient to inhibit or prevent, partially or totally, a viral infection or to reverse the development of a viral infection or prevent or reduce its further progression.

The term "monomer", as used herein, refers to both a molecule comprising one or more polymerizable functional groups prior to polymerization, and a repeating unit of a polymer. A copolymer is said to comprise two or more different monomers.

As used herein, the term "polymer backbone" or "backbone" refers to that portion of the polymer which is a continuous chain, comprising the bonds which are formed between monomers upon polymerization. The composition of the polymer backbone can be described in terms of the identity of the monomers from which it is formed, without regard to the composition of branches, or side chains, off of the polymer backbone. Thus, poly(acrylic acid) is said to have a substituted poly(ethylene) backbone with carboxylic acid (—C(O)OH) groups as side chains.

A "pendant" group is a moiety which forms a side chain or a portion of a side chain attached to the polymer backbone.

The acid-functionalized monomer comprises a pendant acid functional group, such as a carboxylic acid group, a sulfonic acid group, a hydrosulfate group, a phosphonic acid group, a boronic acid group. The acid functional group can also be present in the anionic, or conjugate base, form, in combination with a cation. Suitable cations include alkaline earth metal ions, such as sodium and potassium ions, alkaline earth ions, such as calcium and magnesium ions, and unsubstituted and substituted (primary, secondary, tertiary and quaternary) ammonium ions.

The aliphatic spacer group is a component of the polymer side chain and connects the acid functional group to the polymer backbone. The term "aliphatic" describes a chemical moiety which is not aromatic and does not comprise an aromatic component. The spacer group can be linear, branched or cyclic. Suitable aliphatic spacer groups include normal or branched, saturated or partially unsaturated hydrocarbyl groups, including alkylene groups, for example, polymethylene groups such as —$(CH_2)_n$—, wherein n is an integer from 1 to about 20, and cycloalkylene groups, such as the 1,4-cyclohexylene group. The alkylene group can be substituted or unsubstituted. Suitable alkylene substituents include hydroxyl groups and halogen atoms, for example, fluorine, chlorine and bromine atoms. The alkylene group can also, optionally, be interrupted at one or more points by a heteroatom, such as an oxygen, nitrogen or sulfur atom. Examples include the oxaalkylene groups —$(CH_2)_2O[(CH_2)_2O]_n(CH_2)_2$—, wherein n is an integer ranging from 0 to about 3. The aliphatic spacer group can also be a partially unsaturated group, such as a substituted or unsubstituted $C_2$–$C_{20}$-alkenylene group or a $C_2$–$C_{20}$-alkenylene group interrupted at one or more points by a heteroatom.

The pendant hydrophobic group can be a substituted or unsubstituted, saturated or partially unsaturated $C_2$–$C_{24}$-hydrocarbyl group or a substituted or unsubstituted aryl or arylalkyl group. Examples of suitable alkyl substituents include halogen atoms, such as fluorine or chlorine atoms, and aryl groups, such as a phenyl group. Aryl substituents can include halogen atoms, $C_1$–$C_6$-alkyl groups and $C_1$–$C_6$-alkoxy groups. Preferably, the pendant hydrophobic group is a normal or branched $C_2$–$C_{24}$-alkyl group.

The polymer to be administered is, preferably, a copolymer comprising an acid-functionalized monomer and a hydrophobic monomer. The term "hydrophobic monomer", as used herein, is a monomer which comprises a pendant hydrophobic group, as described above. Suitable hydrophobic monomers include substituted or unsubstituted N-$C_3$–$C_{24}$-alkylacrylamides, such as N-n-decylacrylamide and N-isopropylacrylamide, substituted or unsubstituted $C_3$–$C_{24}$-alkylacrylates, such as n-butylacrylate and n-decylacrylate; and styrene and substituted styrenes, such as pentafluorostyrene and 4-fluorostyrene.

The copolymer can have a wide range of compositions, comprising, for example, from about 10 mole % to about 50 mole % of the hydrophobic monomer, and from about 90 mole % to about 50 mole % of the acid-functionalized monomer.

In one embodiment, the polymer to be administered is characterized by a repeat unit or monomer of the general formula

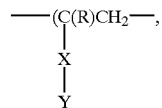

wherein X is an aliphatic spacer group or a direct bond, R is hydrogen or an alkyl group, preferably methyl or ethyl, and Y is an acid functional group. Examples of suitable monomers of this type include acrylic acid, methacrylic acid, 2-ethylacrylic acid, vinylsulfonic acid, vinylphosphonic acid, 3-allyloxy-2-hydroxy-1-propanesulfonic acid, vinylacetic acid and esters of vinyl and allyl alcohol mineral acids, such as sulfuric, phosphoric and boric acids, including vinyl hydrosulfate, vinyl dihydrophosphate, allyl hydrosulfate allyl dihydrophosphate and conjugate bases thereof.

In another embodiment, the polymer to be administered is characterized by a repeat unit or monomer of the general formula

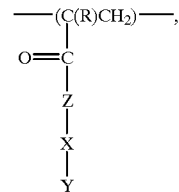

wherein —C(O)—Z—X— is an aliphatic spacer group wherein Z is oxygen or NH and X is an aliphatic group or a direct bond. Y is an acid functional group and R is hydrogen or an alkyl group, preferably methyl or ethyl. Examples of suitable monomers of this type include 2-acrylamidoglycolic acid and 2-acrylamido-2-methyl-1-propanesulfonic acid.

Suitable copolymers for use in the present method include copolymers of acrylic acid and a $C_2$–$C_{20}$-alkylacrylate, such as poly(acrylic acid-co-n-decylacrylate) and poly(acrylic acid-co-n-butylacrylate). Also included are copolymers of acrylic acid and an N-$C_2$–$C_{20}$ alkylacrylamide, such as poly(acrylic acid-co-N-isopropylacrylamide) and poly(acrylic acid-co-N-n-decylacrylamide), and copolymers of acrylic acid with styrene or a substituted styrene, such as pentafluorostyrene or 4-fluorostyrene.

In another embodiment, the polymer to be administered is a copolymer comprising an acid-functionalized monomer, a hydrophobic monomer and a neutral hydrophilic monomer. A neutral hydrophilic monomer is a monomer comprising a polar group which is neither appreciably acidic nor appreciably basic at physiological pH. Examples of suitable neutral hydrophilic monomers include acrylamide, N-(2-hydroxyethyl) acrylamide, N-(3-hydroxypropyl)acrylamide, 2-hydroxyethylacrylate, vinyl acetate, vinyl alcohol and N-vinylpyrrolidone. A suitable copolymer of this type is the terpolymer poly(acrylic acid-co-n-decylacrylate-co-acrylamide).

The polymer to be administered can also be characterized by a repeat unit comprising both a pendant hydrophobic group and a pendant acid functional group. Suitable hydrophobic groups and acid functional groups include those discussed above. Polymers of this type include poly(2-alkylacrylic acid), wherein the alkyl group comprises from 2 to about 24 carbon atoms. One suitable polymer of this type is poly(2-ethylacrylic acid) or a conjugate base thereof. The polymer to be administered can also comprise a first monomer having a pendant hydrophobic group and a pendant acid functional group and a second neutral, hydrophilic monomer, such as the neutral hydrophilic monomers previously discussed.

The polymer to be administered will, preferably, be of a molecular weight which is suitable for the intended mode of administration and allows the polymer to reach and remain within the targeted region of the body. For example, a method for treating an intestinal infection should utilize a polymer of sufficiently high molecular weight to resist absorption, partially or completely, from the gastrointestinal tract into other parts of the body. The polymers can have molecular weights ranging from about 2,000 Daltons to about 500,000 Daltons, preferably from about 5,000 Daltons to about 150,000 Daltons.

The polymers of use in the present method are preferably substantially nonbiodegradable and nonabsorbable. That is, the polymers do not substantially break down under physiological conditions into fragments which are absorbable by body tissues. The polymers preferably have a nonhydrolyzable backbone, which is substantially inert under conditions encountered in the target region of the body, such as the gastrointestinal tract. Polymer backbones which are suitable for the present invention include polyacrylamide, polyacrylate, poly(vinyl) and poly(ethyleneimine) backbones. A co-polymer of the present invention can comprise a combination of two or more of these backbone elements. The polymer to be administered can also be an condensation polymer, such as a polyamide or a polyester.

The quantity of a given polymer to be administered will be determined on an individual basis and will be determined, at least in part, by consideration of the individual's size, the severity of symptoms to be treated and the result sought. The polymer can be administered alone or in a pharmaceutical composition comprising the polymer, an acceptable carrier or diluent and, optionally, one or more additional drugs.

The polymer can be administered by subcutaneous or other injection, intravenously, topically, orally, parenterally, transdermally, or rectally. The form in which the polymer will be administered, for example, powder, tablet, capsule, solution, or emulsion, will depend on the route by which it is administered. The therapeutically effective amount can be administered in a series of doses separated by appropriate time intervals, such as hours.

The polymers of the present invention can be prepared via two general routes, direct copolymerization of a monomer mixture comprising an acid-functionalized monomer and a hydrophobic monomer, and nucleophilic side chain substitution on a activated polymer. The monomer mixture can be polymerized using, for example, methods of free radical, cationic or anionic polymerization which are well known in the art. Due to differences in the reactivity ratios of two or more monomers, the mole ratio of the monomers in the copolymer product can be different from the mole ratio of the monomers in the initial reaction mixture. This reactivity difference can also result in a non-random distribution of monomers along the polymer chain.

Another synthetic route to polymers suitable for the present method proceeds via an intermediate polymer having labile side chains which are readily substituted by a desired side chain. Suitable polymers of this type include poly(N-acryloyloxysuccinimide) (pNAS), which reacts with a primary amine, for example, to form an N-substituted polyacrylamide. Another suitable polymer with labile side chains is poly(4-nitrophenylacrylate), which also forms an N-substituted polyacrylamide upon reaction with a primary amine.

For example, a copolymer with a polyacrylamide backbone comprising amide nitrogen atoms substituted with an acid functional group and amide nitrogen atoms substituted with a hydrophobic group can be prepared by treating pNAS with less than one equivalent (relative to N-acryloyloxysuccinimide monomer) of a primary amine which terminates in an acid functional group, such as an amino acid, for example, glycine. A hydrophobic group can then be introduced by reacting at least a portion of the remaining N-acryloyloxysuccinimide monomers with a second primary amine, such as a $C_2$–$C_{20}$-alkylamine. A co-polymer further comprising a neutral hydrophilic monomer can be prepared by reacting any remaining N-acryloyloxysuccinimide monomers with, for example, 2-aminoethanol or ammonia. A variety of copolymer compositions can, thus, be readily obtained by treating the activated polymer with different ratios of selected amines.

The invention will now be further and specifically described by the following examples.

EXAMPLES

Example 1
Synthesis of Acrylic Acid/Styrene Copolymer (2:1)

A solution was prepared of acrylic acid (15.0 g, 0.2 mol) and styrene (10.4 g, 0.1 mol) in THF (200 mL). After the solution was degassed with a rapid stream of nitrogen, azobis(isobutyrylnitrile) (AIBN, 1.47 g, 3 mol % with respect to total monomer) was added. The solution was degassed for a further thirty minutes and the reaction was then heated to 70° C. for 14 h. The solution was cooled and precipitated into n-hexane (800 mL). The hexane was decanted from the fibrous white product, the product was washed with ethyl acetate (300 mL) followed by washing with a further aliquot of hexane (200 mL). The polymer was dried in vacuo to yield 21.6 g, 84.6% of a brittle white solid.

Example 2
Synthesis of Acrylic Acid/decylacrylate (96:4) Copolymer

A solution was prepared of acrylic acid (10.0 g, 133 mmol) and n-decylacrylate (1.0 g, 4.71 mmol) in dioxane (200 mL). The solution was degassed by passing a rapid stream of nitrogen through it, and to the solution was added AIBN (0.6 g, 5 mol % with respect to total monomer). The solution was degassed for a further thirty minutes and the reaction was then heated to 70° C. for 16 h. The solution was cooled and precipitated into ethyl acetate (600 mL). The ethyl acetate was decanted from the fibrous white product, the product was washed with ethyl acetate (300 mL) and then with hexane (200 mL). The polymer was dried in vacuo to yield 9.0 g, 81% of a brittle white solid.

Example 3
Synthesis of Acrylic Acid/n-butylacrylate (9:1)Copolymer

A solution was prepared of acrylic acid (10.0 g, 133 mmol) and n-butylacrylate (2.0 g, 14.41 mmol) in dioxane (200 mL). The solution was degassed by passing a rapid stream of nitrogen through it, and to the solution was added AIBN (0.6 g, 5 mol % with respect to total monomer). The solution was degassed for a further thirty minutes and the reaction was then heated to 70° C. for 17 h. The solution was cooled and precipitated into ethyl acetate (600 Ml). The ethyl acetate was decanted from the fibrous white product, the product was washed with ethyl acetate (300 Ml) followed by washing with hexane (200 Ml). The polymer was dried in vacuo to yield 9.0 g (81%) of a brittle white solid.

The corresponding polymer of acrylic acid and n-butylacrylate (10:3) was made by the same procedure.

Example 4
Synthesis of Acrylic Acid/n-decylacrylate/acrylamide (70:7.5:22.5) Terpolymer A solution was prepared of acrylic acid (10.0 g, 133 mmol), n-decylacrylate (3.0 g, 14.2 mmol) and acrylamide (3.0 g, 42.2 mmol) in dioxane (200 mL). After the solution was degassed with a rapid stream of nitrogen, AIBN (1.3 g) was added. The solution was degassed for a further thirty minutes and the reaction was then heated to 70° C. for 17 h. The polymer precipitated as a fibrous white solid as the reaction proceeded. The solution was cooled and the dioxane decanted. The residue was washed with ethyl acetate (600 mL) and the ethyl acetate was discarded. The polymer was finally washed with hexanes (300 mL) and dried in vacuo.

Example 5
Synthesis of Acrylic Acid/n-butylacrylate/acrylamide (60:15:25) Terpolymer A solution was prepared of acrylic acid (10.0 g, 133 mmol), n-butylacrylate (4.0 g, 31.4 mmol) and acrylamide (4.0 g, 56.3 mmol) in dioxane (200 mL). After the solution was degassed with a rapid stream of nitrogen, AIBN (1.3 g) was added. The resulting solution was degassed for a further thirty minutes and was then heated to 70° C. for 17 h. As the reaction proceeded, the polymer precipitated as a fibrous white solid. The solution was cooled and the dioxane was decanted. The polymer was washed with ethyl acetate (600 mL), then with hexanes (300 mL) and dried in vacuo.

Example 6
Synthesis of Co-polymer of Acrylic Acid and Decylacrylate (10:2).

A solution was prepared of acrylic acid (10.0 g, 133 mmol) and decylacrylate (5.64 g, 26.6 mmol) in dioxane (300 mL). After the solution was degassed with a rapid stream of nitrogen, AIBN (0.8 g) was added. The resulting solution was degassed for a further thirty minutes and the reaction mixture was heated to 70° C. for 16 h. The solution was cooled and added to ethyl acetate (600 mL). The ethyl acetate was decanted from the resulting fibrous white product. The product was then redissolved in dioxane (150 mL), precipitated with ethyl acetate (500 mL), filtered, washed with cold hexanes (300 mL) and dried in vacuo.

Example 7
In Vitro Assessment of Rotavirus Inhibition Activity

The ability of several compounds to inhibit the infection of cells by rotavirus was assessed via a Focus Forming Unit Assay. The Focus Forming Unit Assay measures the ability of a compound to inhibit primary infection of cells with rotavirus, using the Rhesus Rotavirus strain (RRV). The protocol for the Focus Forming Unit Assay is as follows:

1. MA104 cells ($3 \times 10^4$) were plated in 96 well microtiter plates (Corning) at 3 days before infection. Serial dilutions of polymers to be tested were prepared in Medium 199 in a concentration range between 10 and 0.01 mg/ml and adjusted to pH 7 with 2M NaOH solution.
2. 100 $\mu$l of thawed RRV virus was added to 900 $\mu$l of Medium 199 (Gibco/BRL), followed by the addition of 2.5 $\mu$l of 2 mg/ml trypsin and the solution was incubated at 37° C. for 20 minutes. This process activated the virus for infection.
3. The virus was diluted 1:125 (1:1250 final) in Medium 199 without Fetal Bovine Serum. 250 $\mu$l of diluted polymer and incubated at 37° C. for 1 hour. Controls included mixing virus with media alone and with neutralizing monoclonal antibody.
4. The medium was aspirated from the wells and washed once with 100 $\mu$l of the virus/polymer dilution mixture was added to each well, plating each dilution of polymer in quadruplicate. The plates were incubated on a rocking platform for 20 hours at 37° C.
5. The medium was aspirated from the wells and to the wells was added 100 $\mu$l of 10% Formalin. The plates were incubated 1 hour at room temperature.
6. The cells were permeabilized by adding 1% Triton X100 for 3 minutes, followed by washing twice with Hanks Balanced Salt Solution.
7. 80–100 $\mu$l of primary antibody (DAKO rabbit anti-rotavirus serum diluted 1:250) were added to the wells and incubated at 37° C. for 1 hour on a rocking platform.
8. The wells were washed twice with HBSS followed by the addition of 100 $\mu$l per well of 1:10,000 dilution of peroxidase conjugated anti-rabbit serum (Sigma). The wells were incubated at 37° C. for 1 hour on a rocking platform.
9. The wells were washed twice with HBSS. 100 $\mu$l of AEC substrate (3 amino-9-ethylcarbazole dissolved to 4 mg/ml in dimethylformamide and diluted to 20% in pH 5.2 0.1 M acetate buffer) was then added. After incubating for 20 minutes at room temperature, the reaction was stopped by washing once with HBSS. Infected cells appeared red and were quantified by counting the number of foci relative to control.

The polymers of Examples 2, 3, 5 and 6 were examined via the Focus Forming Unit Assay. Each of these polymers had an $ED_{50}$ (the concentration at which the extent of infection was 50% that of the control) of less than 0.08 mg/mL.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of treating a viral infection in a mammal, comprising administering to the mammal a therapeutically effective amount of a polymer comprising a plurality of pendant hydrophobic groups and a plurality of pendant acid functional groups, said acid functional groups being connected to the polymer backbone by an aliphatic spacer group having a length from 1 to about 20 atoms.

2. The method of claim 1 wherein the polymer is a copolymer comprising an acid-functionalized monomer and a hydrophobic monomer.

3. The method of claim 1 wherein the acid functionalized group is a carboxylic acid, a phosphonic acid, a hydrosulfonic acid, a boronic acid or a conjugate base thereof.

4. A method of treating a viral infection in a mammal, comprising administering to the mammal a therapeutically effective amount of a polymer comprising a monomer of the formula:

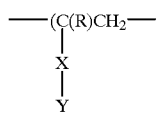

wherein X is an aliphatic spacer group or a direct bond, Y is an acid functional group, and R is hydrogen or alkyl and wherein the acid functionalized group is a carboxylic acid, a phosphonic acid, a hydrosulfonic acid, a boronic acid or a conjugate base thereof.

5. The method of claim 4 wherein the polymer is a copolymer comprising an acid-functionalized monomer and a hydrophobic monomer.

6. The method of claim 5 wherein the virus is selected from the group consisting of influenza virus, rotavirus, Norwalk virus, coronavirus and calicivirus.

7. The method of claim 5 wherein the hydrophobic monomer comprises a $C_2$–$C_{20}$-alkyl group, an arylalkyl group or an aryl group.

8. The method of claim 7 wherein the aliphatic spacer group is a normal or branched, substituted or unsubstituted $C_1$–$C_{20}$-alkylene group or a substituted or unsubstituted $C_1$–$C_{20}$-alkylene group interrupted at one or more points by a heteroatom and the hydrophobic monomer comprises a $C_2$–$C_{20}$ alkyl group.

9. The method of claim 8 wherein the heteroatom is an oxygen, sulfur or nitrogen atom.

10. The method of claim 5 wherein the acid-functionalized monomer is acrylic acid, methacrylic acid, 2-ethylacrylic acid, vinylacetic acid, vinyl hydrosulfate, vinyl hydrophosphate, or a conjugate base thereof.

11. The method of claim 5 wherein the hydrophobic monomer comprises a substituted or unsubstituted aryl or arylalkyl group.

12. The method of claim 11 wherein the hydrophobic monomer is styrene or substituted styrene.

13. The method of claim 5 wherein the polymer further comprises a neutral, hydrophilic monomer.

14. The method of claim 13 wherein the neutral, hydrophilic monomer is selected from the group consisting of acrylamide, N-(2-hydroxyethyl)acrylamide, N-vinylpyrrolidinone, N-hydroxypropylacrylamide, 2-hydroxyethylacrylate, vinylacetate, and vinylalcohol.

15. A method of treating a viral infection in a mammal, comprising administering to the mammal a therapeutically effective amount of a polymer comprising a monomer the formula:

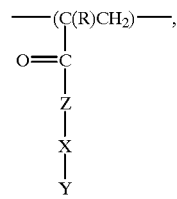

wherein X is an aliphatic spacer group, Y is an acid functional group, Z is an oxygen atom or an NH group, and R is hydrogen or alkyl.

16. The method of claim 15 wherein the polymer is a copolymer comprising an acid-functionalized monomer and a hydrophobic monomer.

17. The method of claim 16 wherein the aliphatic spacer group is a normal or branched, substituted or unsubstituted $C_1$–$C_{20}$-alkylene group or a substituted or unsubstituted $C_1$–$C_{20}$-alkylene group interrupted at one or more points by a heteroatom and the hydrophobic monomer comprises a $C_2$–$C_{20}$ alkyl group.

18. The method of claim 16 wherein the heteroatom is an oxygen, sulfur or nitrogen atom.

19. The method of claim 18 wherein the hydrophobic monomer is selected from the group consisting of $C_2$–$C_{20}$-alkylacrylates, $C_2$–$C_{20}$-alkylmethacrylates, $C_2$–$C_{20}$-alkylethacrylates, N-$C_2$–$C_{20}$-alkylacrylamides, N-$C_2$–$C_{20}$-alkylmethacrylamides and N-$C_2$–$C_{20}$-alkylethacrylamides.

20. The method of claim 15 wherein the hydrophobic monomer comprises a substituted or unsubstituted aryl or arylalkyl group.

21. The method of claim 15 wherein the polymer further comprises a neutral, hydrophilic monomer.

* * * * *